United States Patent [19]

Young

[11] Patent Number: 4,826,009

[45] Date of Patent: May 2, 1989

[54] CONTAINER ASSEMBLY

[75] Inventor: George Young, Libertyville, Ill.

[73] Assignee: The Kendall Company, Boston, Mass.

[21] Appl. No.: 225,506

[22] Filed: Jul. 28, 1988

Related U.S. Application Data

[63] Continuation of Ser. No. 86,761, Aug. 18, 1987, abandoned.

[51] Int. Cl.⁴ .............................................. B65D 85/42
[52] U.S. Cl. .................................... 206/440; 206/438; 206/441; 128/156
[58] Field of Search ............... 206/438, 440, 441, 828, 206/813; 128/156

[56]   References Cited

U.S. PATENT DOCUMENTS

| | | | |
|---|---|---|---|
| Re. 30,843 | 1/1982 | Flint | 206/813 |
| 608,921 | 8/1898 | Silverman | 128/156 |
| 706,250 | 8/1902 | Muller | 128/156 |
| 2,682,266 | 6/1954 | Freiberger | 206/441 |
| 3,007,571 | 11/1961 | Marinaro | 206/441 |
| 3,122,142 | 2/1964 | Crowe, Jr. | 128/156 |
| 3,152,694 | 10/1964 | Nashed et al. | 206/440 |
| 3,338,019 | 8/1967 | Trewella et al. | 206/440 |
| 3,438,371 | 4/1969 | Fischer et al. | 128/156 |
| 3,487,832 | 1/1970 | Spence | 128/156 |
| 3,491,753 | 1/1970 | Milton et al. | 206/440 |
| 3,530,494 | 9/1970 | Baratta | 206/441 |
| 3,618,756 | 11/1971 | Trewella | 206/440 |
| 3,653,502 | 4/1972 | Beaudoin | 206/440 |
| 3,670,731 | 6/1972 | Harmon | 128/156 |
| 4,557,381 | 12/1985 | Whitney | 206/440 |
| 4,564,108 | 1/1986 | Widlund et al. | 206/438 |

FOREIGN PATENT DOCUMENTS 1242232  12/1959  France .................. 206/438

Primary Examiner—David T. Fidei
Attorney, Agent, or Firm—Emrich & Dithmar

[57]    ABSTRACT

A container assembly comprising, a dressing, a base sheet placed on one side of the dressing of a material relatively non-adherent to the dressing, and a cover sheet placed on the other side of the dressing of a material relatively adherent to the dressing.

4 Claims, 1 Drawing Sheet

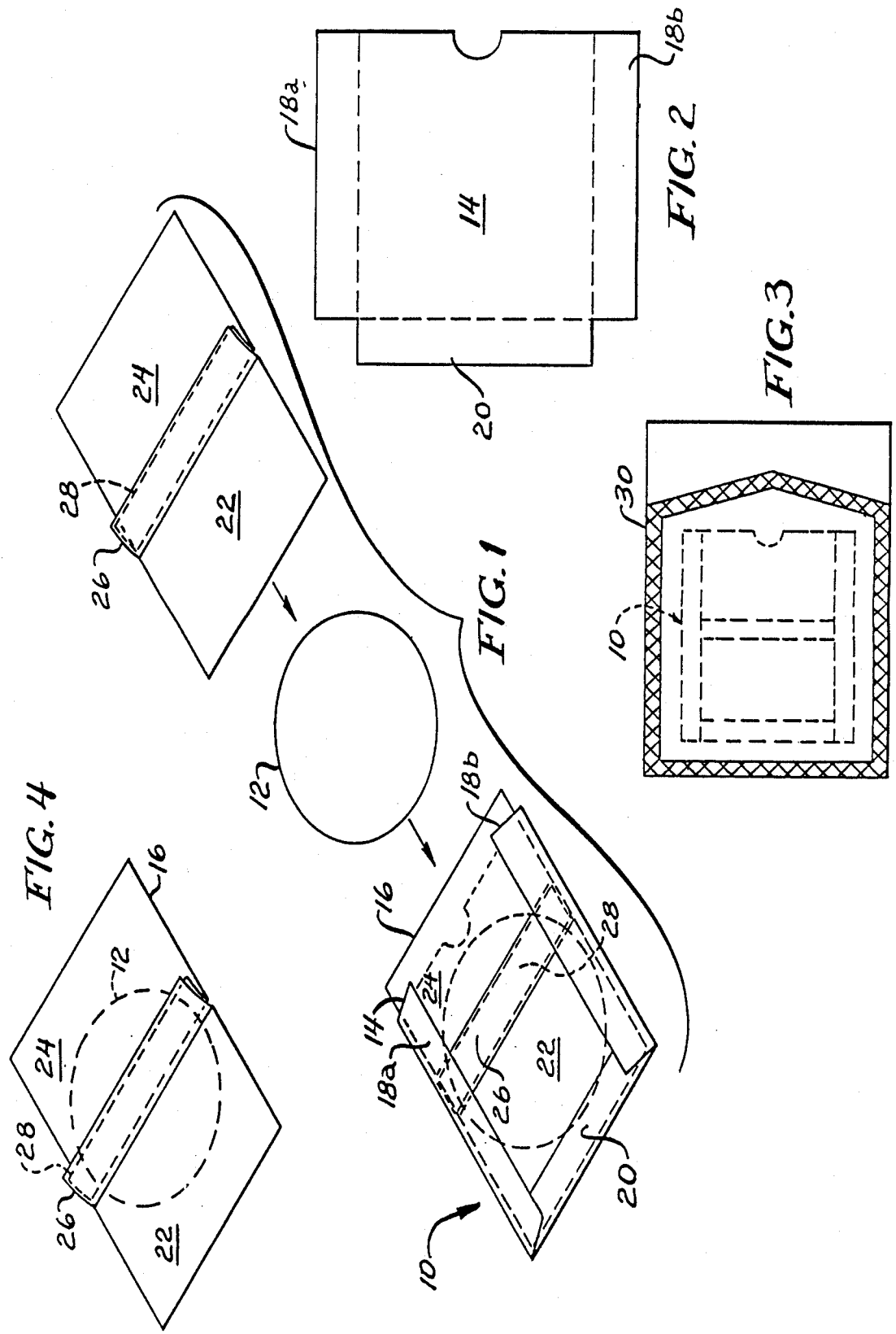

CONTAINER ASSEMBLY

This is a continuation of application Ser. No. 086,761, filed Aug. 18, 1987, now abandoned.

BACKGROUND OF THE INVENTION

The present invention relates to container assemblies for surgical dressings.

Before the present invention, surgical dressings have been retained in a sterile condition in packages. However, the dressings have a tendency to adhere to the packages, thus making it difficult to place them in the package and remove them from the package.

SUMMARY OF THE INVENTION

A principal feature of the present invention is the provision of a container assembly.

The container assembly comprises, a dressing, a base sheet placed on one side of the dressing of a material relatively non-adherent to the dressing, and a cover sheet placed on the other side of the dressing of a material relatively adherent to the dressing.

A feature of the present invention is that the container assembly may be readily placed in and removed from an outer sterile package.

Another feature of the invention is that the base sheet may have a plurality of side and end flaps to hold the cover sheet in proper position over the dressing.

Yet another feature of the invention is that the cover sheet and dressing may be readily removed from the base sheet while the dressing adheres to the cover sheet.

Still another feature of the invention is that the cover sheet may be utilized to place the dressing over a wound.

Yet another feature of the invention is that the cover sheet may be peeled from the dressing with the dressing in place on the wound.

A feature of the present invention is that the dressing may be removed from the package and placed in a sterile manner.

Further features will become more fully apparent in the following description of the embodiments of this invention and from the appended claims.

DESCRIPTION OF THE DRAWINGS

In the drawings:

FIG. 1 is an exploded perspective view of a container assembly of the present invention;

FIG. 2 is a plan view of a base sheet for the assembly of FIG. 1;

FIG. 3 is a plan view of a package for the container assembly of FIG. 1; and

FIG. 4 is a perspective view illustrating use of the cover sheet for placement of a dressing in the container assembly.

DESCRIPTION OF THE PREFERRED EMBODIMENTS

Referring now to FIGS. 1 and 2, there is shown a container assembly generally designated 10 having a dressing of known type, a base sheet 14 placed on one side of the dressing 12, and a cover sheet 16 placed on the other side of the dressing 12. The base sheet 14 is constructed from a material which is relatively non-adherent to the dressing 12, such as silicone release paper. The base sheet 14 has a pair of flaps 18a and 18b adjacent opposed sides of the base sheet 14, and a flap 20 adjacent one end of the base sheet 14. As shown, the cover sheet 16 is substantially coextensive with the base sheet 14, and the flaps 18a and b and 20 are folded over the cover sheet 16 in order to retain the cover sheet 16 in place over the dressing 12. In a preferred form, the cover sheet 16 has a pair of segments 22 and 24, with each of the segments 22 and 24 having a lateral strip 26 and 28 located adjacent each other over the dressing 12. The cover sheet 16 is constructed from a material which is relatively adherent to the dressing 12, such as polyethylene.

As shown in FIG. 3, the container assembly 10 is received in a cavity 32 of a package 30. The package 30 is sealed around its periphery in order to maintain the dressing 12 in a sterile condition in the package 30.

According to the present invention, the container assembly 10 may be placed in the package 30, and may be readily removed from the package 30 in preparation for use. Thus, the container assembly 10 is removed from the package 30 while the flaps 18a and b and 20 prevent dislodgement of the cover sheet 16 from the base sheet 14. After removal of the container assembly 10 from the package 30, the cover sheet 16 is removed from the base sheet 14 while the cover sheet 16 retains the dressing 12 due to the adherence of the cover sheet 16 for the dressing 12, while the base sheet 14 permits easy removal of the dressing 12 from the base sheet 14 due to its non-adherence to the dressing 12. With reference to FIG. 4, the cover sheet 16 retaining the dressing 12 is placed over a wound of a patient, and the strips 26 and 28 are peeled from the dressing 12 in order to remove the cover sheet 16 from the dressing 12 with the dressing 12 in place on the wound. In an alternative form, the cover sheet 16 may be constructed from a single sheet of material which is placed in the base sheet 14 over the dressing 12 in a manner as previously described.

The foregoing detailed description is given for clearness of understanding only, and no unnecessary limitations should be understood therefrom, as modifications will be obvious to those skilled in the art.

What is claimed is:

1. A container assembly, comprising:
   a dressing;
   a base sheet placed on one side of the dressing of material relatively non-adherent to the dressing and being free of sealing relationship with itself;
   a cover sheet placed on the other side of the dressing of a material relatively adherent to the dressing and readily removable from the dressing; and
   a package having a cavity to receive the dressing, base sheet, and cover sheet, said package enclosing and being separate from said dressing, base sheet, and cover sheet, wherein the base sheet has a pair of flaps adjacent opposed sides, and a flap adjacent one end, said flaps being folded over the cover sheet.

2. The assembly of claim 1 wherein said base sheet is constructed from a silicone coated release paper.

3. The assembly of claim 1 wherein the cover sheet comprises a polyethylene film.

4. The assembly of claim 1 wherein the cover sheet has a pair of sheet segments, with each of the segments having a lateral strip located adjacent each other to peel the segments from the dressing.

* * * * *